(12) United States Patent
Humphrys et al.

(10) Patent No.: US 9,760,684 B2
(45) Date of Patent: Sep. 12, 2017

(54) CAREGIVER CENTRIC AND ACUITY ADAPTING MULTI-PATIENT SYSTEM

(71) Applicant: KONINKLIJKE PHILIPS N.V., Eindhoven (NL)

(72) Inventors: John Francis Humphrys, Needham, MA (US); Larry Nielsen, Burlington, MA (US); Youssef Abou-Hawili, Andover, MA (US); Marianne Messina, Newburyport, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/440,611

(22) PCT Filed: Nov. 5, 2013

(86) PCT No.: PCT/IB2013/059906
§ 371 (c)(1),
(2) Date: May 5, 2015

(87) PCT Pub. No.: WO2014/072900
PCT Pub. Date: May 15, 2014

(65) Prior Publication Data
US 2015/0254412 A1    Sep. 10, 2015

Related U.S. Application Data

(60) Provisional application No. 61/725,041, filed on Nov. 12, 2012.

(51) Int. Cl.
*A61B 5/04*    (2006.01)
*A61B 5/00*    (2006.01)
(Continued)

(52) U.S. Cl.
CPC ...... *G06F 19/3406* (2013.01); *A61B 5/02055* (2013.01); *A61B 5/0402* (2013.01);
(Continued)

(58) Field of Classification Search
USPC .................................................. 600/300–301
See application file for complete search history.

(56) References Cited

U.S. PATENT DOCUMENTS

2003/0050801 A1    3/2003   Ries et al.
2005/0242946 A1   11/2005   Hubbard, Jr. et al.
(Continued)

OTHER PUBLICATIONS

ASCOM Wireless Solutions; 2006; www.ascom.com/ws accessed Sep. 18, 2012.
IBM_UPMC_Smartcom; 2010; ibm.com/smarterplanet/healthcare Accessed Sep. 18, 2012.

*Primary Examiner* — Nicole F Johnson

(57) ABSTRACT

A workflow system includes a workflow unit (8), a location unit (10), and a display device (12). The workflow unit (8) identifies and tracks patient assessment and patient vital signs for a plurality of patients each assigned to at least one caregiver according to a schedule for each patient. The location unit (10) receives a location of each assigned caregiver and a location of each patient. The display device (12) displays grouped, caregiver centric, acuity adapted, clinical data, and crucial timing information for each patient in a consistent format as well as a name and the location of the patient, a caregiver name and the caregiver location for each assigned caregiver.

20 Claims, 6 Drawing Sheets

Figure 1:
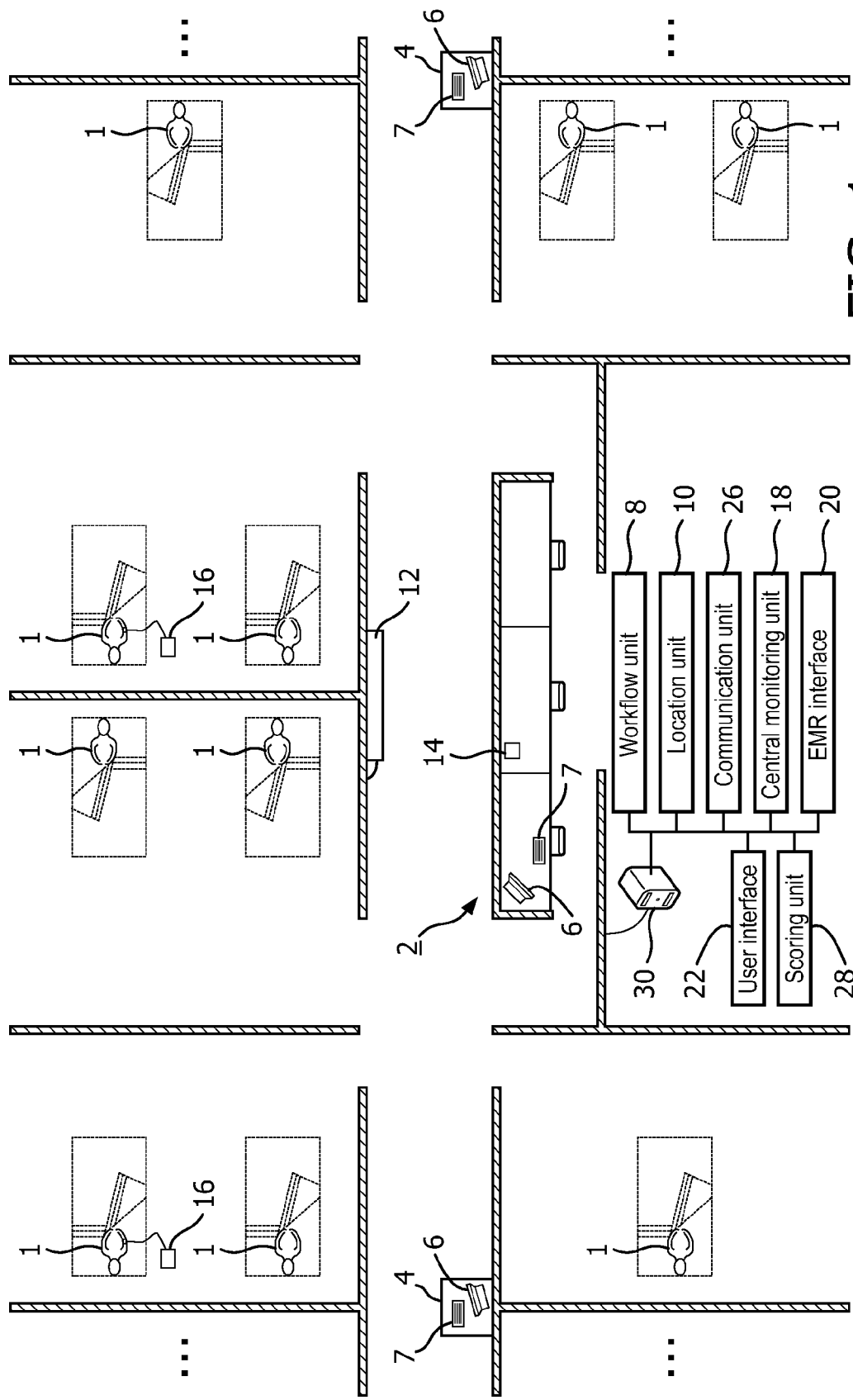

(51) Int. Cl.
*G06F 19/00* (2011.01)
*G06Q 50/24* (2012.01)
*A61B 5/0205* (2006.01)
*A61B 5/0402* (2006.01)
*A61B 5/145* (2006.01)
A61B 5/021 (2006.01)
A61B 5/024 (2006.01)
A61B 5/08 (2006.01)

(52) U.S. Cl.
CPC ...... *A61B 5/14532* (2013.01); *A61B 5/14542* (2013.01); *A61B 5/746* (2013.01); *A61B 5/7435* (2013.01); *G06F 19/327* (2013.01); *G06Q 50/24* (2013.01); A61B 5/021 (2013.01); A61B 5/024 (2013.01); A61B 5/0816 (2013.01); *G06F 19/322* (2013.01)

(56) References Cited

U.S. PATENT DOCUMENTS

| | | |
|---|---|---|
| 2008/0235057 A1 | 9/2008 | Weidenhaupt et al. |
| 2009/0132580 A1 | 5/2009 | James et al. |
| 2010/0131292 A1 | 5/2010 | Hawkins et al. |
| 2010/0222649 A1* | 9/2010 | Schoenberg ........ G06F 19/3418 600/301 |
| 2011/0245630 A1 | 10/2011 | St. Pierre et al. |
| 2012/0119890 A1 | 5/2012 | Collins, Jr. et al. |
| 2012/0179479 A1* | 7/2012 | Waterson ............... G06Q 50/22 705/2 |

* cited by examiner

531B Albert — Vitals Started: 9:45 — ⧖ 0:16
- LOC: ☒ Person ☒ Place ☒ Time
- NIBP ?
- Temp 98.6
- HR ?
- Glu 117 — 07:45 / 11:45
- Resp 18
- SpO2 ?
- 531 Marianne RN | 533 Katherine

532A Johnson — Vitals Started: 9:52 — ⧖ 7:08
- LOC: ☒ Person ☒ Place ☒ Time
- NIBP ?
- Temp ?
- HR ?
- Glu 86 — 07:32 / 11:45
- Resp ?
- SpO2 ?
- 539 Susan RN | 533 Katherine

533 Adams — Vitals Started: 9:49 — ⧖ 4:32
- LOC: ☒ Person ☒ Place ☒ Time
- NIBP ?
- Temp ?
- HR 68
- Glu 116 — 07:20 / 11:45
- Resp ?
- SpO2 97
- 530 Mary Ann RN | 533 Katherine

534 Smoot
- LOC: ? Person Place Time
- NIBP ?
- Temp ?
- HR ?
- Glu 120 — 07:37 / 11:45
- Resp ?
- SpO2 ?
- 531 Marianne RN | 533 Katherine

536B Smith — Vitals Completed: 9:59 — Next Vitals: 17:00
- LOC: ☒ Person ☒ Place ☒ Time
- NIBP 122/80 (88)
- Temp 98.6
- HR 67
- Glu 90 — 07:45 / 11:45
- Resp 18
- SpO2 95
- 531 Marianne RN | 534 Katherine

FIG. 2

CAREGIVER CENTRIC AND ACUITY ADAPTING MULTI-PATIENT SYSTEM

CROSS REFERENCE TO RELATED APPLICATIONS

This application is a national filing of PCT application Serial No. PCT/IB2013/059906, filed Nov. 5, 2013, published as WO 2014/072900 A1 on May 15, 2014, which claims the benefit of U.S. provisional application Ser. No. 61/725,041 filed Nov. 12, 2012 which is incorporated herein by reference.

The following relates generally to patient care systems. It finds particular application in conjunction with nursing and/or clinical workflow and patient monitoring, and will be described with particular reference thereto. However, it will be understood that it also finds application in other usage scenarios and is not necessarily limited to the aforementioned application.

An acute care unit, such as an intensive care unit (ICU), typically includes 10-30 high acuity patients and in the U.S. averages about 15 patients. Patients are monitored continuously by monitors, which are often automated and can include central monitoring systems. A nurse who is typically assigned a limited number, e.g. 2, patients continuously assesses the patient and performs any vital sign measurement or other measurement not automated. Assessment by the nurse of the patient level of consciousness (LOC) includes orientation by the patient to their name, location, and date and/or time. Each bed is typically equipped with any monitoring equipment needed. The nurse is nearby, typically in one or at most 2 rooms, usually in visual distance. Communication between the nurse and any other caregiver and/or healthcare practitioner is facilitated by the close proximity to the patient, e.g. without having to find the nurse and/or use electronic communication. The nurse, sometimes with the assistance of an aide provides all of the services typically needed while in the acute care unit.

Patients leave the ICU and enter lower acuity or mixed care healthcare environments such as a step-down unit, mixed care unit, etc. The lower acuity healthcare environments include general hospital wards, medical/surgical floors, emergency rooms, day-surgery units, and the like through other means, and sometimes transition between several areas before discharge as the patient monitoring and/or caregiving needs change or diminish. With lower acuity areas, the ratio of patients to caregivers changes, the caregiver team member roles typically vary, the type and quantity of monitoring equipment change, and the type and frequency of monitoring each patient changes. For example, a clinical care floor typically has 20-60 patients and in the U.S. an average of about 30 patients. Nurses are typically assigned 5-6 patients and nurse aides are typically assigned about 12 patients. Vital signs and routine measurements are performed on all patients. Vital signs include non-invasive blood pressure, temperature, heart rate, respiration rate, $SpO_2$, etc. Routine measurements can include glucose monitoring typically performed 15 minutes before the patient eats. The schedule of taking vital signs can vary from continuous to several hours to once or twice each shift and can vary with each patient. The role of the nurse is focused on patient assessments, special procedures, and medications, but can still include obtaining vital signs and other measurements. The role of the aide includes obtaining vital signs, changing bed linens, glucose testing or other measurements, and assisting with activities of daily living (ADLs). The nurses and aides are more mobile with supporting larger patient groups, and locating and communicating between the caregivers and other healthcare practitioner becomes more difficult.

Equipment for monitoring is typically shared in the lower acuity patient areas. For example, non-invasive blood pressure (NIBP) monitors are typically mobile and transported to each patient to be measured. Continuous monitors may be used on some patients, but are less likely to be part of a central monitoring system. The monitoring equipment used is less likely to provide automated measurements. Nurses or aides may enter assessment or measurement information into an Electronic Medical Record (EMR) through an electronic computing device such as a computer. The device may be found in each room, but may be located in a common area such as a hallway or at a central nursing station.

When a caregiver obtains the assessment and/or measurement, the caregiver will typically login to the EMR, locate the patient's records and enter the results. The caregiver can view results or history of an individual patient. The caregiver logs out of the system and then proceeds to the next patient. There is no overall system perspective of patient workload for which a nurse or nurse aide is responsible. There is no view of the activities to be done based on the variety of patient schedules by each caregiver, e.g. a "todo" list. For example, a first patient may need vital signs taken every two hours, and a glucose measurement prior to the time of being served their next meal. A second patient may need vital signs taken every four hours, but does not need their glucose measured. A third patient may need their vital signs taken every hour and their glucose measured prior to their next meal. There is no view with all three patients.

Patient assignments to nurses and aides for a shift are typically noted on a dry erase board or whiteboard. At the beginning of a shift the nurses and aides receive their assignments and review the charts of their assigned patients to identify the various schedules for assessment, vital sign measurements, glucose measurements, etc. for each patient. Aides are typically assigned contiguous rooms to enable them to easily go from room to room to care for and assist patients. However, nurses are less likely to be assigned contiguous rooms because of variation in skill levels and patient requirements.

The patient care environment is a dynamic environment where different events occur which interrupt tasks. Patients generate events such as reactions to food, medicine, or condition changes. Addressing the different events and keeping the various schedules can prove difficult. The nurse and/or a supervisor balance the workload by identifying who is behind in their tasks and asking other caregivers to help with the outstanding tasks. Workload balancing is difficult because there is no list of tasks to be performed according to the various patient schedules, and the caregivers are mobile which complicates locating and communicating with the caregivers. Team communication plays a vital role. Some healthcare facilities do not have an infrastructure which supports direct caregiver communication, which means going from room to room to locate a particular caregiver or paging the caregiver who may be involved in another task. The schedules are organized by individual patient and dictated by patient acuity. The outstanding tasks may vary in the skill requirements, e.g. require an assessment which cannot be performed by an aide.

The variability in patient acuities, schedules and equipment needs drives the need for patient transfers to different areas such as ICUs to step-down wards to general wards. The transfers include a cost and difficulty of moving a patient. Sometimes as many as nine healthcare practitioners are involved in a single patient transfer. However, the ICU systems and equipment are not oriented to the change in acuity, mobility, and cost of resources involved in a universal bed model where the patient remains in the same location until discharge.

The following discloses a new and improved caregiver centric and acuity adapting multi-patient system which addresses the above referenced issues, and others.

In accordance with one aspect, a workflow system includes a workflow unit, a location unit, and a display device. The workflow unit identifies and tracks patient assessment and patient vital signs for a plurality of patients each assigned to at least one caregiver according to a schedule for each patient. The location unit receives a location of each assigned caregiver and a location of each patient. The display device displays grouped, caregiver centric, acuity adapted, clinical data, and crucial timing information for each patient in a consistent format as well as a name and the location of the patient, a caregiver name and the caregiver location for each assigned caregiver.

In accordance with another aspect, a method of caregiver workflow includes assigning at least one caregiver to each of a plurality of patients. Patient assessment and patient vital signs are identified and tracked for each patient. The at least one caregiver location is tracked and indicated. A name and the location of the patient, a caregiver name and the caregiver location for each assigned caregiver are displayed grouped for each patient in a consistent format.

One advantage is workflow centricity and specificity to each individual caregiver.

Another advantage resides in an ability to provide workload balancing of caregiver workloads.

Another advantage resides in the support of team communication including a nurse and aide assigned to a particular patient, between nurses, aides and/or supervisors on a floor or other healthcare unit.

Another advantage resides in adaptability to different levels of acuity from the ICU to discharge.

Another advantage resides in an ability to provide timing indicators of key activities that must be completed or are already overdue.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a caregiver centric and acuity adapting system.

FIG. 2 illustrates an example of a caregiver workflow display.

Figure 3:
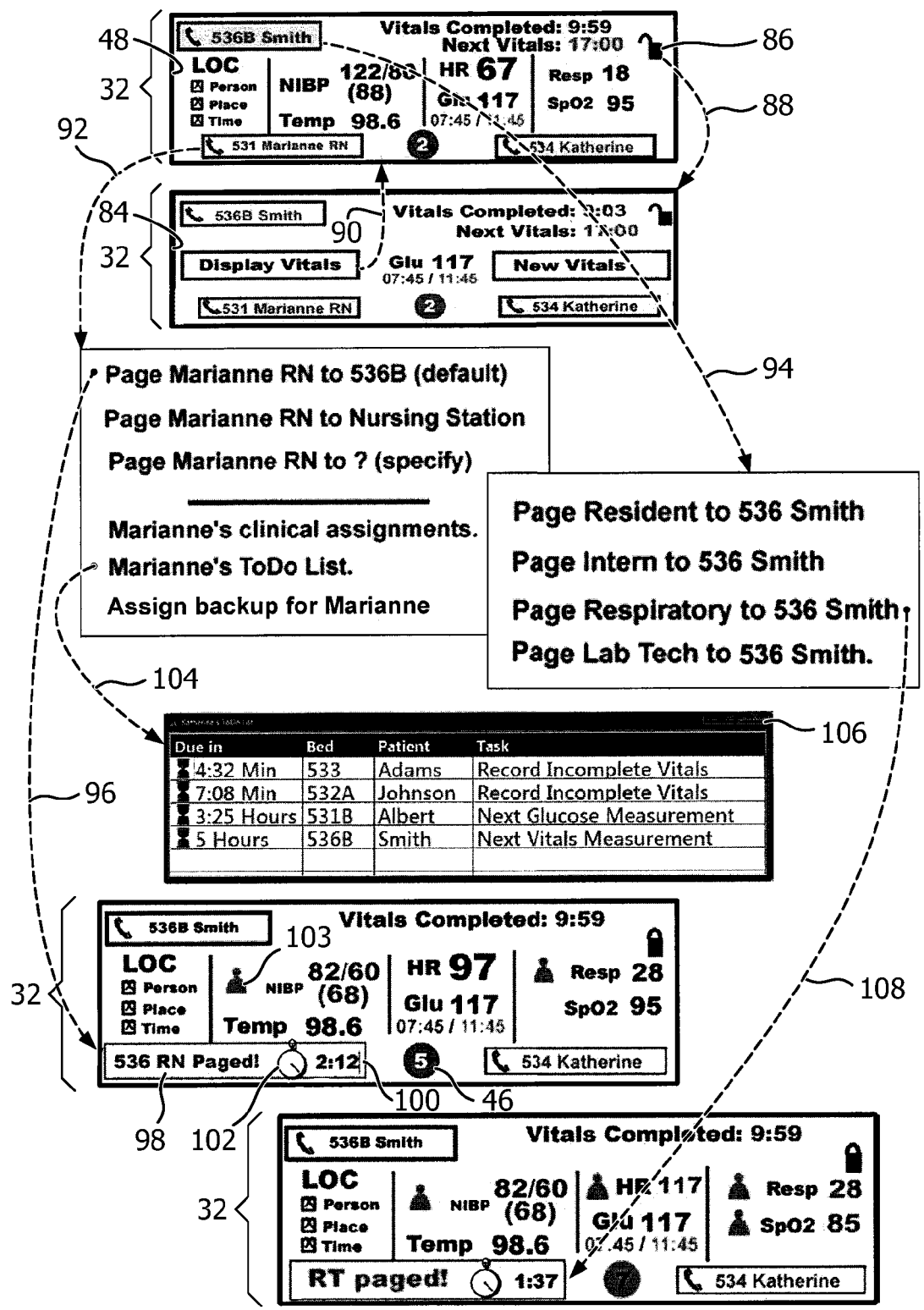

FIG. 3 diagrammatically illustrates examples of workflow visualization.

Figure 4:
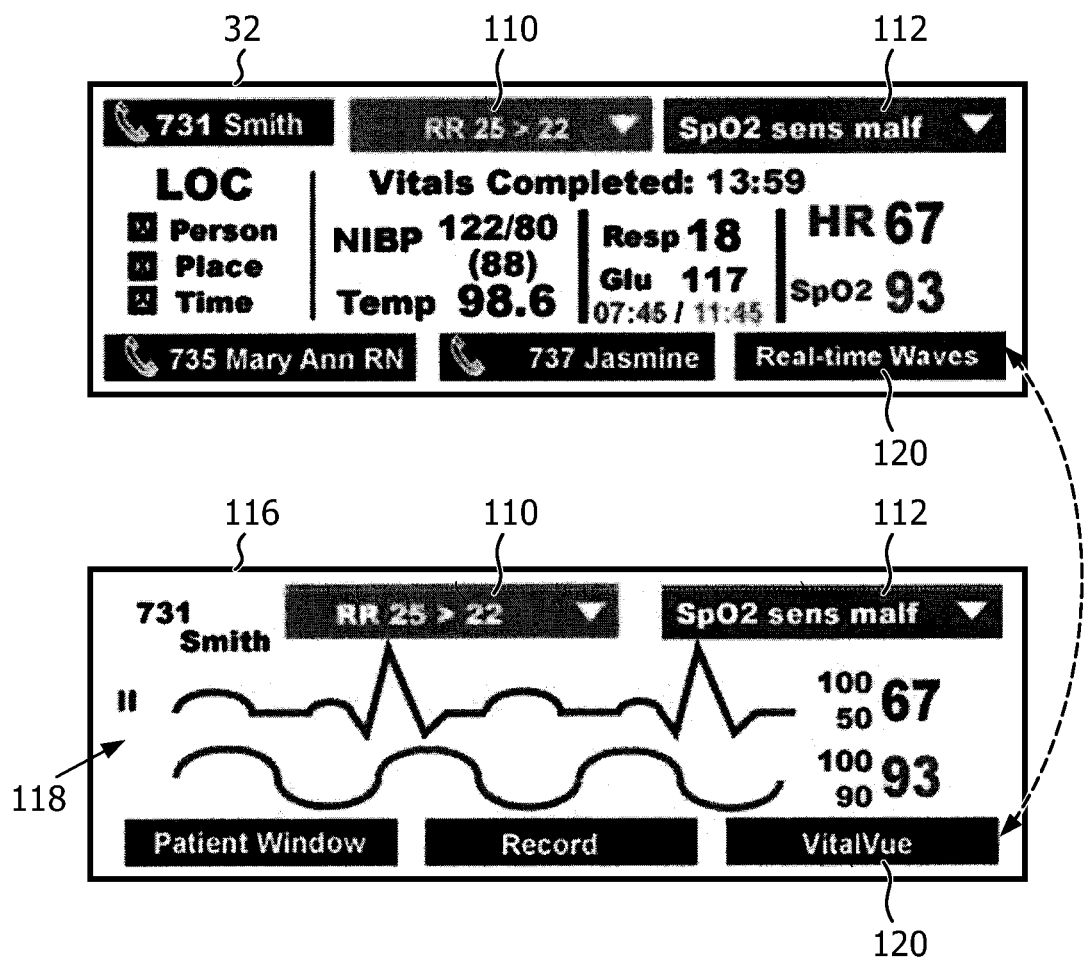

FIG. 4 illustrates an example of workflow integration with other systems.

Figure 5:
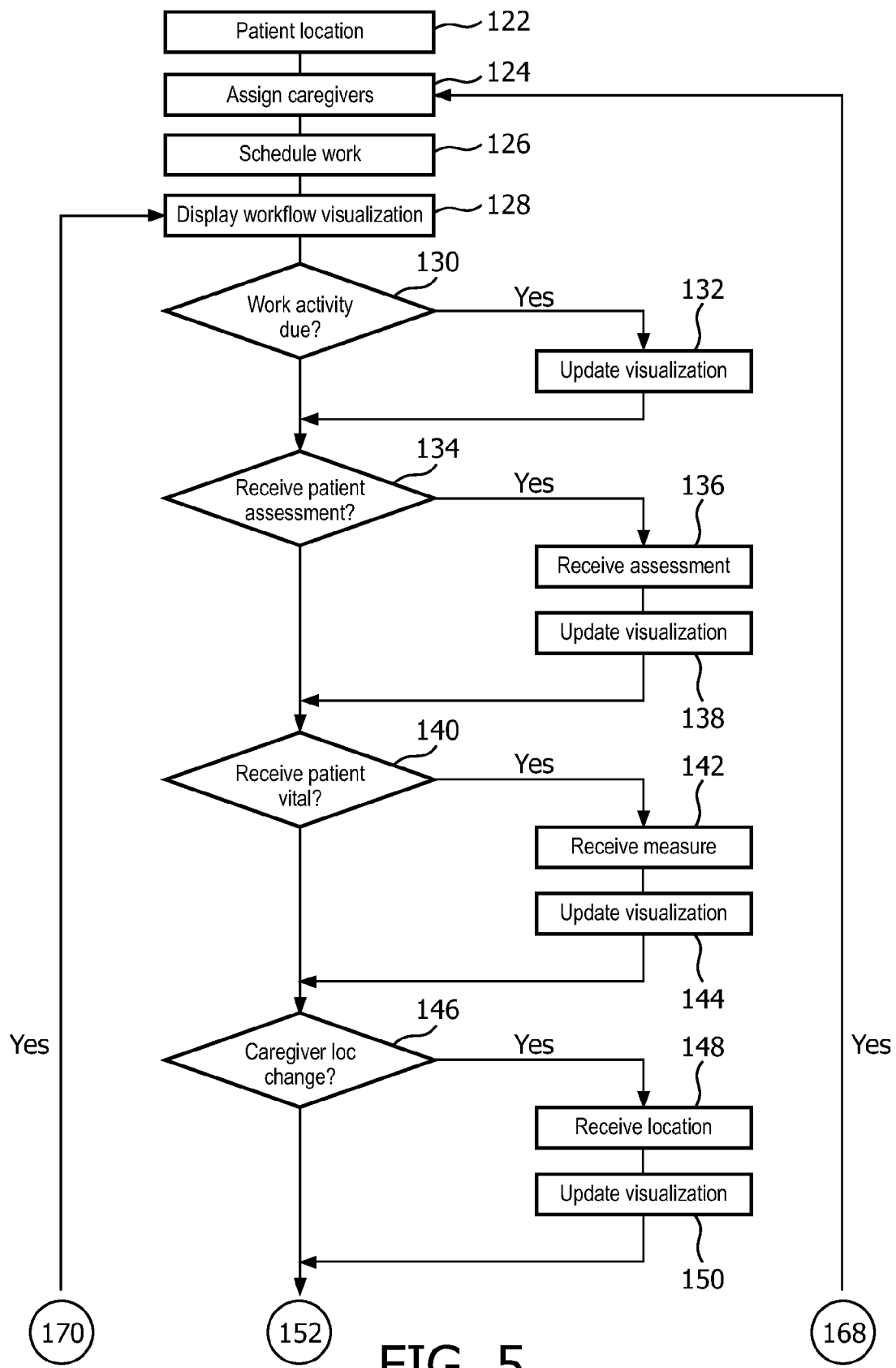
Figure 5:
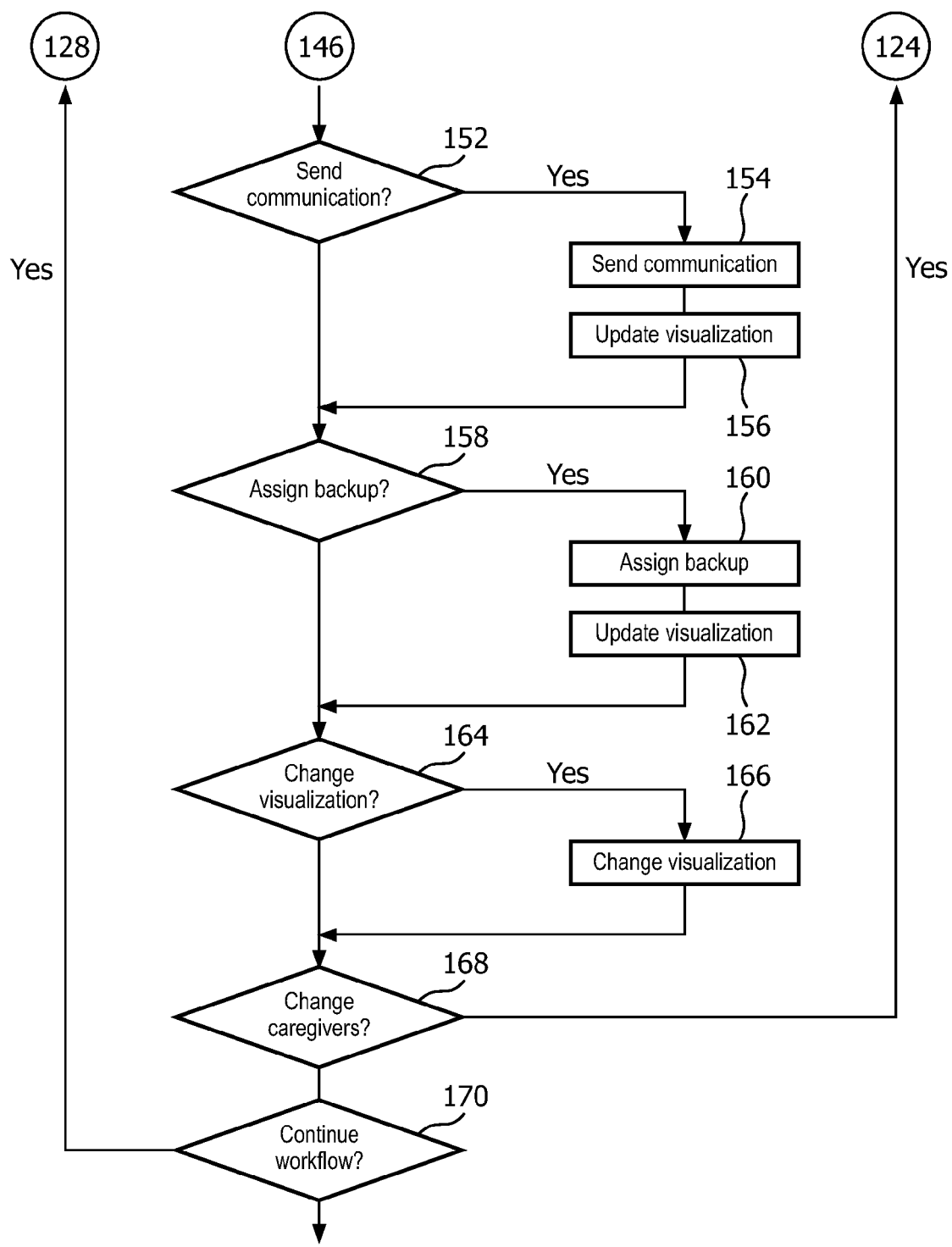

FIG. 5 flowcharts one method of using an embodiment of caregiver centric and acuity adapting system.

With reference to FIG. 1, an embodiment of caregiver centric and acuity adapting system is schematically illustrated in a patient clinical care unit such as a general ward, step-down unit, mixed care unit, medical/surgical floor, etc. The clinical care unit includes a plurality of patients 1 and one or more nursing stations. The nursing stations can be a centralized location 2 or be distributed across the care unit such as hallway stations 4. The nursing stations can include a workstation 6 or other computing device with a user interface 22 for entry of patient assessment and vital signs, other information, and display of workflow. The workstations include at least one input device 7 such as a keyboard and/or mouse. Alternatively, rooms and/or bedsides can be equipped with a workstation or other computing device.

The system includes a workflow unit 8, a location unit 10, and a display device 12. The workflow unit receives the assignments of nurses and nurse aides to the plurality of patients. For example, a nurse Marianne is assigned to patients in rooms 529, 531, 536, and 538. A nurse Susan is assigned to patients in rooms 532, 535, 539-540. A nurse Mary Ann is assigned to patients in rooms 530, 533-534, and 537, and a nurse Mike is assigned to patients in rooms 527-528, and 541-542. A nurse aide Katherine is assigned to patients rooms 530-539. A nurse aide Erica is assigned to patients in rooms 520-529 and a nurse aide Carla is assigned to patients in rooms 540-549. The workflow unit retrieves each patient name and location based on previously stored information such as a hospital information system or other clinical system to obtain a patient name and specific location. The specific location includes those rooms with multiple patients such as semi-private, triples, quads, etc. where the patient location includes the room number and other designation such as the room number and a letter, e.g. 533A, 533B, etc. The workflow unit can include assigning a backup for a particular nurse or aide which is given effect during breaks.

The workflow unit 8 identifies and tracks patient assessment and patient vital signs according to the schedule for each patient. Patient schedules are based on patient acuity as dictated by doctor orders. The schedules determined the time for each patient assessment to be performed by a nurse and the taking of patient vital signs by a nurse aide or nurse. For example, a patient located in 533A is to be assessed and vital signs measured every 2 hours. A patient located in 533B is to be assessed and vital signs measured twice per shift.

Patient assessments must be performed by a nurse. Patient assessment includes a level of consciousness (LOC) assessment of person, place, and time. Patient assessment can include other assessments such as neurological Glaus Glaucoma assessment performed on neurological patients, and the like. Measurement of patient vital signs includes non-invasive systolic and diastolic blood pressure, temperature, a heart rate, a respiration rate, and a SpO$_2$ measurement. The blood pressure can include a mean blood pressure. The measurement can include other measures such as a glucose measure for specific patients and according to a different schedule than vital signs measured with measuring device 14 such as a glucose meter. Measures can include for some patients telemetry measured by an individual patient monitor 16 and/or received by a central monitoring unit 18. Patient assessments and measures are entered by the nurse and/or aide automatically or manually using a workstation 6 and/or a mobile computing device such as a personal device appliance (PDA). The assessment and/or measures can be entered into an Electronic Medical Record (EMR) and retrieved using the EMR interface unit 20 or directly into the workflow unit using a user interface 22. The workflow unit generates an event for each assessment and/or measurement of a vital sign or other measure with a due time. The due time is tracked by the workflow unit. The workflow unit generates a visualization of the workflow for the assigned caregivers.

The location unit 10 receives the location of each caregiver, e.g. nurse and aide. The location can be tracked by a variety of techniques which include the caregiver wearing a radio frequency identification device (RFID), GPS device, or via manual login tracking at the workstation, etc. During backup periods such as breaks the location unit can receive the location of the backup caregiver to an aide or nurse.

The display device 12 can include a workstation 6 display and/or a separate wall display such as a flat panel display, a computer monitor, a television screen, a touch screen, Cathode ray tube (CRT), Light-emitting diode (LED) displays, Electroluminescent display (ELD), Plasma display panels (PDP), Liquid crystal display (LCD), Organic light-emitting diode displays (OLED), personal display appliances carried by the caregivers, and the like. The display device displays grouped for each patient a visualization of the identified and tracked patient assessments and vital sign measurements. The visualization can include other identified and tracked measurements such as glucose. The visualization includes a consistent format with the assessment and measurements separated. The visualization includes a name and location of the patient, a name and location of each assigned caregiver, e.g. nurse and/or aide.

The system includes a communication unit 26 and can include a scoring unit 28. The communication unit 26 communicates an electronic page to a caregiver with a command. For example, tapping on the caregiver's name automatically pages a) the assigned caregiver or b) the nurse closest to the patient if the assigned caregiver happens to be in a remote zone such as cafeteria or bathroom or c) both the assigned caregiver and the alternate caregiver. The communication unit tracks an elapsed time from a time of the electronic page, and the visualization is updated to show that the page has been sent and to show the elapsed time. The electronic page can include a message which pages the caregiver to a specific room location, to the nursing station, or a location entered by a healthcare practitioner. The page can also be sent to other healthcare practitioners such as a respiratory therapist (RT), lab technician (LT), and the like.

The scoring unit 28 generates an Early Warning Score (EWS) based on the entered assessment and/or measurements. The scoring unit can utilize scoring as reported in the literature, or be customized to a specific implementation. The EWS is designed to provide a numeric representation indicative of the current state of the patient. For example, a score can range from 1-7 where 1 represents a patient in good condition and 7 represents a patient in critical condition. The EWS can be included for each patient in the visualization by the workflow unit and displayed by the display device. The EWS score can include color to emphasize differences in scoring such as green for normal, red for critical, and yellow for cautious and can be utilized to automatically trigger clinician and/or team communication.

The various units or interfaces 8, 10, 18, 20, 22, 24, 26, and 28 are suitably embodied by an electronic data processing device, such as the electronic processor or electronic processing device of the workstation 6, or by a network-based server computer 30, or so forth. The user interface(s) 22 are suitably embodied by the workstation 6 or PDA(s). Moreover, the disclosed workflow and visualization techniques are suitably implemented using a non-transitory storage medium storing instructions (e.g., software) readable by an electronic data processing device and executable by the electronic data processing device to perform the disclosed workflow and visualization techniques.

FIG. 2 illustrates an example of a caregiver workflow display. Information about each patient is grouped in a consistent format for ease and speed of understanding. The grouped information for each patient can be organized into a rectangle area called a sector 32. Each sector includes a patient name 34 and patient location 36 in a common location such as the upper left corner where reading occurs left to right and top to bottom. Each sector includes a name of the nurse 38 assigned to the patient and the current location of the nurse 40 as received by the location unit. Each sector can include a name of the aide 42 assigned to the patient and the current location of the aide 44 as received by the location unit. In other embodiments, caregivers in other roles can be included such as residents, interns, RTs, LTs, and the like. Each sector can include the EWS 46 as calculated by the scoring unit based on the last vital signs.

Sectors can be categorized as patient assessment and vital sign measurements completed 48, patient assessment and vital sign measurements started but not completed 50, or patient assessment and measurements overdue 52. Patient assessment and measurements completed include a time of last completion 54 and a next scheduled time to be completed 56. Completed patient assessments and/or measurements include the values and/or indications of completion. For example, a LOC patient assessment 58 can be visualized using check boxes, one box each for person, place, and time. A check mark indicates a successful result. An "x" or "-" can indicate the assessment performed, but the patient has not reached the LOC aspect. A blank box or a question mark indicates the assessment is outstanding. Each measurement of the patient vital signs includes a value where completed such as NIBP systolic/diastolic/mean level 60, temperature 62, heart rate 64, respiration rate 66, $SpO_2$ level 68, and the like. The sector can include a glucose level 70 or other measurement. The glucose or other measure can be according to a different schedule and include a different time of last completion 72 and a different next time to be completed 74.

The sector with started but not completed patient assessment and vital sign measurements 50 includes an indicator for the assessment or values for measured vital signs and an indicator for missing items such as a "?" mark. The workflow unit sets a time according to a pre-determined period such as 15 minutes in which the assessment and vital sign measurements are to be completed. If the assessment and/or vital signs are not completed with the pre-determined period, then the process of making the assessment and/or taking the vital signs is restarted. With the entry or receiving by the workflow unit, a timer is started for time remaining in the pre-determined period of time. The time is counted down. In the visualization, the time of the first measurement vital sign and/or assessment aspect 78, the time remaining 80, and a time remaining icon 82 are displayed. The sector with overdue patient assessment and vital sign measurements 52 includes visual indicators which show which values or assessments are missing.

The visualization co-locates the patient assessment 58 with the assigned nurse 40. The visualization co-locates the measurements 60, 62, 64, 66, 68, 70 usually performed by the aide with the assigned aide 42. The co-location and the sector format allow each caregiver to quickly identify assigned tasks centric to the assigned caregiver role.

FIG. 3 diagrammatically illustrates examples of workflow visualization. Sectors with completed assessment and vital signs 48 can alternatively be displayed as sectors with completed assessment and vital signs without non-critical information 84. A locking mechanism 86 visualized by a lock icon indicates whether the sector without non-critical information is displayed instead of the sector with the completed assessment and vital signs 48. The locking mechanism in the locked mode maintains the completed assessment and vital sign visualization 48. The locking mechanism in the unlocked mode as indicated by an unlocked lock icon transitions 88 after a pre-determined period of time to the sector without non-critical information displayed 84. The locking mechanism can be enabled/disabled with an input command such as a right click of a mouse. Non-critical information includes vital sign measurements which are considered normal. The vital signs can be displayed by transitioning 90 back from the sector without non-critical information display to the sector with the completed assessment and vital signs 48. The transition can be based on an input command such as a right mouse click or a tap on a "display vitals" button. General information such as an EWS score or other measurement can be configured to display in both types of sectors. Reducing the amount of information displayed adapts the caregiver centric sector display to different levels of patient acuity and improves the speed and clarity of the remaining tasks.

Additional commands and/or transitions can be performed. The commands can be context dependent upon the visualization of information. For example, a right click or a tap on an assigned caregiver name displays a menu of options 92 related to the assigned caregiver. In another example, a right click or a tap on a patient name displays a menu of options 94 related to the patient. The options for a caregiver dependent context can include send an electronic page to the caregiver to come to the patient room, nursing station, or other specified location. The commands reduce data entry errors. Selecting the option to send the electronic page sends the page using the communication unit 26 and transitions 96 the visualization of the sector to include an indicator that the caregiver has been paged 98, and displays the time elapsed 100 since the page was sent and an elapsed time icon 102. For example, a healthcare practitioner such as another caregiver enters the vital signs which indicate a low NIBP and a fast respiration rate. Optional icons indicating an alarm condition 103 are set for measured values below a threshold amount for the patient. The healthcare practitioner right clicks or taps the assigned nurse and selects paging the nurse to the patient location. The sector is updated to display that the page is sent for the nurse and the elapsed time. The display provides team communication that the nurse has been page and how long ago the page was sent. The display reduces the need for team members to repeatedly ask if the nurse has been paged. The display indicates how long the page has been sent before another team member needs to intervene. The menu options preconfigured to send specific page reduce error and ensure that a page is properly sent.

In another selection from the menu of options for the assigned caregiver is to display a "To Do" list for the caregiver. For example, by selecting the To Do list option 104 based on the context dependent selection of the caregiver, a list of tasks remaining for the caregiver 106 is displayed ordered by the time due of the tasks with earliest time due first. For example, the tasks for a nurse include performing vital sign measurements for two patients where the assessments were completed but not the vital signs. The time remaining before restart of the assessment and vital signs for a patient Adams is 4:32 min. A second patient Johnson has 7:08 min before restart of the patient assessment and vital signs. Patient Albert has 3:25 hours before the next glucose measurement, and patient Smith has 5 hours before his/her next vital signs measurements. Adams is shown first, followed by Johnson, Albert, and then Smith in order of when the task is due. Color can be used to further enhance the display such as red for tasks due in less than 5 minutes, yellow for tasks due within 30 minutes, and green for the remaining tasks.

Other menu options related to the assigned caregiver include review and/or update of clinical assignments and assigning a backup. The assignment function can be limited to supervisory personnel and/or delegated to individual caregivers. Clinical assignments can be changed on a caregiver by caregiver basis or be assigned as a shift rotation. Backup assignments provide substitution of other caregivers when the assigned caregiver is on break, but maintain the assignment and return the assigned caregiver to the visualization once the break is ended.

The menu options related to the patient 94 can include the page sent to other caregivers such as respiratory therapists, interns, residents, lab technicians, and the like to come to the patient based on the sector selected. Similar to the paging the nurse or aide, after selecting a menu option to page a caregiver 108 the sector is updated to display a message indicating which caregiver is paged, the elapsed time since the page sent, and the elapse time icon. The elapsed time icon 102 and the time remaining icon 82 provide clarification to the displayed time. A third different icon such as a clock face indicates a scheduled time which differs from the elapsed time and time remaining. The sectors show three types of time: (1) time remaining indicated by the hour glass icon 82, 2) elapsed time since an event indicated by the stopwatch icon 102, and (3) scheduled time with or in a clock icon either in digital or analog format.

FIG. 4 illustrates an example of workflow integration with other systems such as a central monitoring system. For example, an alarm 110 such as a respiratory rate past a threshold is visualized within the patient sector 32 and the source of the alarm is a central monitoring system, telemetry monitor, and the like. Alarm of a non-functioning monitoring device 112 can also be included in the visualization.

The visualization of the sector includes the ability to change the format of the visualization to include a sector format 116 of the central monitoring system which provides a waveform 118 visualization of vital signs. The sector format can be displayed instead of the workflow sector 32 for each patient. Some patients can include the waveform display while other patients who are not continuously monitored display one of the workflow sector formats. The transition between the workflow sector can include a command such as a visualized button 120 which toggles between the different formats.

FIG. 5 flowcharts one method of using an embodiment of caregiver centric and acuity adapting workflow. In a step 122, patient names and locations are received. The patient names and locations can be received from the EMR interface 20 or by entry from the user interface 22. The caregivers are assigned to each patient in a step 124. The assignment includes at least one caregiver such as a nurse and can include other caregivers such as aides, respiratory therapist, lab technicians, interns, residents, or any other healthcare practitioner assigned ongoing care to patients. The assignment can be based on room numbers, range of room numbers, or individual patients. The assignment can be made for each caregiver for immediate effect, or at a specific time, or can include a shift rotation for a group of caregivers which takes effect at a specific time.

The workflow unit identifies and tracks patient assessment and patient vital signs for each patient according to the schedules for each patient in a step 126. For each patient, each assessment and each measurement of a vital sign or other measurement is identified and scheduled. The workflow unit creates events for assessment and/or measurements. The workflow unit tracks the last completed assessment and/or measurement and the next scheduled assessment and/or measurement. The workflow unit visualizes the identified and tracked assessment and measurements grouped for each patient in a consistent format such as a sector.

The display device 12 displays the visualization for the patients in a step 128. The visualization includes sectors according to display parameters. A default selection display parameter can include a display of all patients, but can be modified with system preferences and/or an entered parameter. The sectors can be ordered according to display parameters. A default order can include patient room, but can be modified with system preferences and/or an entered parameter.

In a series of steps which are repeated, the system checks for events, receives the event, modifies the visualization, and displays the modified visualization. In a step 130, the workflow unit checks identified and tracked tasks to determine tasks which are due. For tasks which are due, the workflow unit modifies the visualization to indicate an assessment or measurement is outstanding in a step 132. The visualization can be modified using an indicator such as a question mark to illustrate outstanding or missing values.

In a step 134, a receiving of a patient assessment is checked. The patient assessment is entered by the nurse automatically or manually using a workstation 6, PDA, etc. via the user interface 22 in a step 136. Alternatively, the nurse can enter the assessment into an EMR and the assessment can be received from the EMR. If the assessment is the first of the assessment and vital signs within the pre-determined period, then the time remaining timer is set. If the assessment completes the assessment and measurements for the pre-determined period, then the timer is removed, the time of last measurement is set, and the time for the next measurement is set. The visualization is modified with the received assessment, and any timer or time changes in a step 138.

A receiving of a patient measurement such as a vital sign measure, glucose measure, or other measure is checked in a step 140. The measure is received in a step 142. If the measure is the first of the assessment or measure for the scheduled measures, then the time remaining timer is set. If the measure completes the measures and/or assessment according to the schedule, then the timer is removed, the time of last measurement is set, and the time for the next measurement is set. For example, if a blood pressure measure is received as the first measurement and/or assessment, then the time remaining timer is set and the assessment and other vital signs are indicated as outstanding such as with a "?" mark. If the blood pressure measure received is not the first received measure or assessment aspect, then only the value is updated. If the blood pressure measure received is the last of the assessment and vital signs, then the blood pressure measure is updated, the timer removed, the time for the last measurement is set and the next time of measurement is set. In another example, a glucose measure is received. The glucose is a single measure in the scheduled measures, e.g. scheduled separately from vital signs and LOC assessment. The measured value of glucose level is updated, the last time of measurement is set, and the next time for measurement is set. The visualization is modified with the received measure, and timer or time changes in a step 144.

A change in caregiver location is checked in a step 146. The change is received from the location unit in a step 148. In a step 150, the visualization of sectors of patients assigned to the caregiver is modified to include the new location received by the location unit. If the patient is transferred to a new location, the current clinical assignments may remain or be updated based on unit protocol.

In a step 152, a sending or a receiving of a communication is checked. The communication unit 26 sends the communication and provides notice in a step 154 that a communication has been sent, identifies the caregiver, and the time when the electronic page or other communication sent. The communication unit sets a timer which measures elapsed time from the time the communication is sent. The receiving includes the answering of a page by a caregiver indicated by an entered command. The visualization is modified in a step 156. The modification includes an identification to whom the communication is sent such as a caregiver which localizes the identification within one or more sectors. For example, if a nurse is paged to a patient room, then only the sector visualized for that patient is modified. If a nurse is paged to the nursing desk, then all the sectors which include the nurse are modified. The scope of sectors modified is based on the context of the communication and is configurable to an embodiment. The receiving of a communication includes removing the elapsed timer. The visualization is modified in a step 156 for a sent communication and/or a received communication. For a sent communication, the sectors within the scope of the communication are modified with a message that a page has been sent to a particular caregiver and an elapsed timer set shown with an elapsed timer icon. For a received communication, the sectors within the scope are modified to display the caregiver name and location, and the message, the elapsed timer and the elapse time icon are removed.

In a step 158, a back-up assignment or removal is checked. The assignment or removal is performed in a step 160. The assignment of a backup can include a time for effect such as only during breaks which are scheduled for a specific time or for effect based on an entered command. For example, Alice can be assigned to be a backup for Marianne during her breaks. When Marianne takes a break, Marianne enters a command that indicates the start of a backup period which modifies the assignments during the backup period to Alice. At the end of the backup period, Marianne can enter a command and the assignments are re-assigned back to Marianne. Alternatively, Marianne's breaks are scheduled for 10:00-10:15, 12:30-1:30, and 3:30-3:45. At the start of each break period, Marianne's assignments are assigned to Alice and at the end of each break period, the assignments are returned to Marianne. The visualization of the assignment changes during the break period is modified in a step 162. The visualization includes the substitution and/or addition of the backup caregiver to the visualization labels of each caregiver name in each sector. For example, Alice can be substituted for Marianne or the label can include both such as Marianne/Alice.

In a step 164, a change in visualization parameters, timers, and/or visualization integration is checked. The change is received in a step 166 and can include a change in order and/or selection of sectors. The change can include information received from a central monitoring unit, telemetry device, etc. such as alarm conditions and/or waveforms. The change can include an update of any elapse time or time remaining timers. The change can include updating colors based on any timer. The change can be specific to a display device or applied to all displays. The change in order of the sectors or selection of sectors from the user interface 22 can include an order and/or selection by patient, nurse, aide, caregiver role, backup assignee, EWS, completed/uncompleted assessment, measured/unmeasured value, elapsed timer, time remaining timer, schedule time, alarm, or a combination. The visualization based on the changed parameters, timers, or visualization integration is modified in a step 168. The visualization includes a modification of the sectors selected and/or the order of the sectors based on the parameters. The visualization can be for a specific sector based on a received integration change such as an alarm, device malfunction, and/or waveform display. The visualization can include different timer values and/or colors.

In a step 168, a change in caregiver is checked. If a change is received the method returns to the earlier step 124 where assignments are made. The process repeats in a decision step 170 which returns to displaying the visualization in the earlier step 128 where the workflow as visualized with sectors is displayed and proceeds with checking for events.

It is to be appreciated that in connection with the particular illustrative embodiments presented herein, certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A workflow system, comprising:
    a workflow unit configured to identify and track patient assessment and patient vital signs for a plurality of patients each assigned to at least one caregiver according to a schedule for each patient;
    a location unit configured to receive a location of each assigned caregiver and a location of each of the plurality of patients; and
    a display device configured to display grouped, caregiver centric, acuity adapted, clinical data for each of the plurality of patients in a consistent format, the clinical data including heart rate and SpO2, and a name and the location of each of the plurality of patients, a caregiver name and the caregiver location for each assigned caregiver, the display further configured to display at least one of:
        an indicator of a result of a last patient assessment, values for patient vital signs last measured, a time of completion for the last assessment and vital sign measurement, and a scheduled time for a next patient assessment and vital sign measurement;
        an indicator of patient assessments and vital signs that are past due; or
        a start time of an assessment or a vital signs measurement, an indicator of a result of the assessment or at least one measured value of the vital signs, an indicator for each outstanding assessment or measured vital sign, and a time remaining in a period to complete the assessment and vital sign measurement.

2. The system according to claim 1, wherein the workflow unit is further configured to identify and track glucose measurement for at least one patient.

3. The system according to claim 1, wherein the at least one assigned caregiver includes both a nurse and an aide.

4. The system according to claim 1, wherein the display device is further configured to display:
    an indicator that a last patient assessment and values for patient vital signs last measured were non-critical, a time of completion for the last assessment and vital sign measurement, and a scheduled time for a next patient assessment and vital sign measurement.

5. The system according to claim 1, wherein the display device is further configured to display a patient assessment which includes a level of consciousness (LOC) assessment of person, place, and time.

6. The system according to claim 1, further including:
    a communication unit configured to communicate an electronic page to at least one assigned caregiver based on the visualization of the assignment and tracks an elapse time from a time of the electronic page; and
    wherein the display device is configured to include in the visualization an indication of the electronic page and the elapsed time.

7. The system according to claim 1, further including:
    a communication unit configured to page at least one caregiver based on an input device selecting an icon associated with the name of the at least one caregiver from the displayed caregiver names displayed on the display device.

8. The system according to claim 1, wherein the display device is further configured to display at least one of:
    an Early Warning Score (EWS);
    a visual indicator of an alarm received from a center monitoring system; or
    a visual indicator of a monitoring device malfunction.

9. The system according to claim 1, wherein the display device is further configured to display a link to a display of at least one waveform of a patient vital sign.

10. The system according to claim 1, wherein:
    the display device is further configured to display time with an elapsed time icon, a time remaining icon, and a scheduled time icon; and
    the elapsed time, time remaining and scheduled time icons are different from each other.

11. The system according to claim 1, wherein the workflow unit is further configured to generate a list of outstanding tasks and time remaining for a selected assigned caregiver.

12. A method of caregiver workflow, comprising:
assigning at least one caregiver to each of a plurality of patients;
tracking a location of the at least one caregiver; and
displaying grouped caregiver centric, acuity adapted, clinical data for each patient in a consistent format a name and the location of the patient, a caregiver name and the caregiver location for each assigned caregiver, the displaying including at least one of:
  displaying an indicator of a result of a last patient assessment, values for patient vital signs last measured, a time of completion for the last assessment and vital sign measurement, and a scheduled time for a next patient assessment and vital sign measurement;
  displaying an indicator of patient assessments and vital signs that are past due; or
  displaying a start time of assessment and vital signs measurement, an indicator of a result of at least one assessment or at least one measured value of the vital signs, an indicator for each outstanding assessment or measured vital sign, and a time remaining in a period to complete the assessment and vital sign measurement; and
wherein displaying the clinical data includes displaying patient vital signs, a patient identifier, a patient location, identification of the at least one caregiver assigned to the patient and a location of each caregiver grouped in sectors by patient for each of the plurality of patients.

13. The method according to claim 12, wherein the method further includes displaying an indication of a caregiver that is a nurse and displaying an indication of a caregiver that is an aide.

14. The method according to claim 12, further including:
communicating an electronic page to at least one assigned caregiver based on the visualization of the assignment; and
modifying the visualization to include an indication of the electronic page and an elapsed time.

15. The method according to claim 12, further including at least one of:
identifying and tracking glucose measurement for at least one patient;
displaying a time and at least one of an hourglass icon, a stopwatch icon, or a clock face icon;
calling or paging a selected caregiver by touching the selected caregiver name on the display;
displaying a waveform of patient vital signs;
displaying an early warning score (EWS); or
displaying a time since an alarm.

16. The system according to claim 1, where the display device is configured to display:
an indicator of a result of a last patient assessment, values for patient vital signs last measured, a time of completion for the last assessment and vital sign measurement, and a scheduled time for a next patient assessment and vital sign measurement.

17. The system according to claim 1, where the display device is configured to display:
an indicator of patient assessments and vital signs that are past due.

18. The system according to claim 1, where the display device is configured to display:
a start time of an assessment or a vital signs measurement, an indicator of a result of the assessment or at least one measured value of the vital signs, an indicator for each outstanding assessment or measured vital sign, and a time remaining in a period to complete the assessment and vital sign measurement.

19. The system according to claim 1, where the display device is configured to display an Early Warning Score (EWS) based on the values for patient vital signs last measured.

20. A workflow system, comprising:
one or more processors configured to:
  identify and track patient assessment and patient vital signs for a plurality of patients according to a schedule for each patient, each patient being assigned to a nurse and an aide; and
  receive a current location of each assigned nurse and aide; and
a display device which displays caregiver centric, acuity adapted, clinical data, grouped for each patient a visualization of a patient identifier, an assessment and vital signs, and a name and the current location of each assigned nurse and aide, the display further configured to display at least one of:
  an indicator of a result of a last patient assessment, values for patient vital signs last measured, a time of completion for the last assessment and vital sign measurement, and a scheduled time for a next patient assessment and vital sign measurement;
  an indicator of patient assessments and vital signs that are past due; or
  a start time of an assessment or a vital signs measurement, an indicator of a result of the assessment or at least one measured value of the vital signs, an indicator for each outstanding assessment or measured vital sign, and a time remaining in a period to complete the assessment and vital sign measurement.

* * * * *